Figure 1:
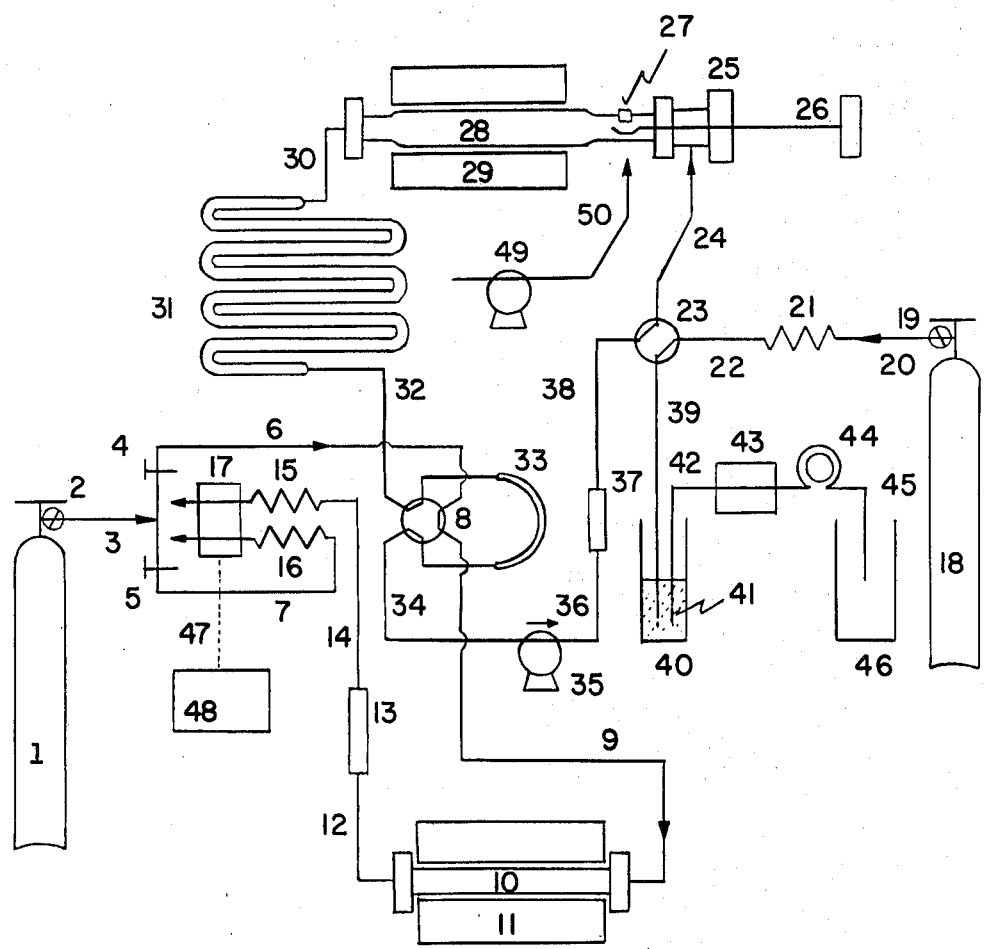

United States Patent [19]

Itoh

[11] 4,401,763
[45] Aug. 30, 1983

[54] ANALYTICAL METHOD FOR THE DETERMINATION OF NITROGEN, CARBON, HYDROGEN AND SULFUR OR CHLORINE AND APPARATUS THEREFOR

[75] Inventor: Tadamasa Itoh, Toyonaka, Japan

[73] Assignee: Sumitomo Chemical Company, Limited, Osaka, Japan

[21] Appl. No.: 318,406

[22] Filed: Nov. 5, 1981

[30] Foreign Application Priority Data

Nov. 13, 1980 [JP] Japan .................. 55-160418

[51] Int. Cl.³ .......................................... G01N 31/12
[52] U.S. Cl. ..................................... 436/115; 422/78; 422/80; 436/123; 436/124; 436/144; 436/145; 436/158; 436/159; 436/160
[58] Field of Search .................. 23/230 PC, 232 C; 422/78, 80; 436/115, 123, 124, 144, 145, 155, 158, 159, 160

[56] References Cited

U.S. PATENT DOCUMENTS

| | | | |
|---|---|---|---|
| 3,304,159 | 2/1967 | Hinsvark | 422/78 X |
| 3,650,696 | 3/1972 | Eads | 23/230 PC |
| 3,698,869 | 10/1972 | Condon | 23/230 PC |
| 3,716,334 | 2/1973 | Pont | 23/230 PC |
| 3,838,969 | 10/1974 | Dugan | 23/230 PC |
| 3,920,396 | 11/1975 | Schuy | 23/230 B |
| 4,227,887 | 10/1980 | Takahashi et al. | 23/230 PC |
| 4,234,315 | 11/1980 | Scott | 422/78 X |
| 4,325,907 | 4/1982 | Dembicki, Jr. et al. | 23/232 C X |

*Primary Examiner*—Arnold Turk
*Attorney, Agent, or Firm*—Birch, Stewart, Kolasch & Birch

[57] ABSTRACT

An analytical method for the independent or simultaneous determination of any number of elements selected from the group consisting of nitrogen, carbon, hydrogen and sulfur or chlorine in samples, which comprises passing an oxygen gas through a reaction tube packed with an oxidation catalyst or oxidizing agent having a heating zone of from 800° C. to 1100° C., introducing a sample into said tube to subject it to complete combustion, uniformalizing the gas, dividing the gas into two portions, and introducing one portion in a carrier gas into a copper-reducing tube having a heating zone of from 400° C. to 700° C., determining the resulting nitrogen gas, carbon dioxide gas and steam or acetylene gas on a gas detector, while introducing the second portion in an oxygen gas into an absorption liquor, and determining the resulting sulfate or chlorine ion and, an apparatus useful therefor.

13 Claims, 3 Drawing Figures

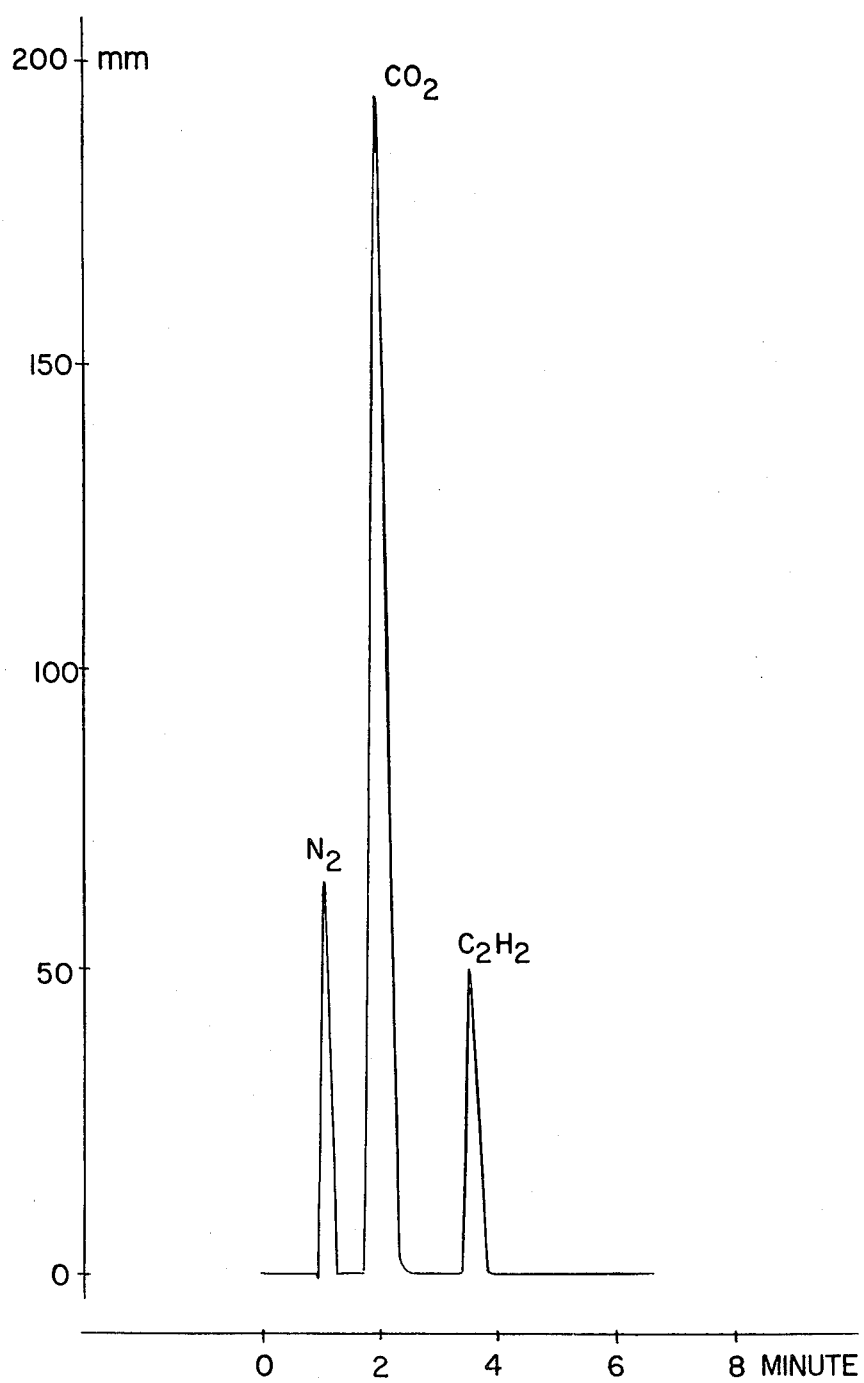

ANALYTICAL METHOD FOR THE DETERMINATION OF NITROGEN, CARBON, HYDROGEN AND SULFUR OR CHLORINE AND APPARATUS THEREFOR

The present invention relates to an analytical method for the elementary determination and an apparatus therefor. More particularly, it relates to an analytical method for the independent or simultaneous determination of any number of elements, nitrogen (N), carbon (C), hydrogen (H) and sulfur (S) or chlorine (Cl) in solid or liquid samples, and an apparatus useful for the elementary analysis.

In the conventional analyzers for elements (C, H, N) in organic substances, it is essential that micro- or ultramicro-balances be used since the maximum weight of a sample to be weighed is from 2 to 3 mg. Since, however, installation of these balances is affected by vibration, air current, humidity, temperature and the like, the balances can not necessarily be installed in all places. Also, because of trace amounts of samples being weighed, it sometimes occurs that errors in weighing lead to poor results, and that samples suitable for analysis can not be obtained. With flame-resisting samples, accurate results occasionally can not be obtained because of incomplete combustion. Further, in determination of trace components such as nitrogen in fuels (e.g. heavy oil, coal) and soils, the above conventional analyzers are not suitable for microanalysis in terms of sensitivity, because the determinable lower limit of nitrogen content is 0.3 wt.%. When a larger amount of sample is used for raising the sensitivity, incomplete combustion takes place on account of a deficiency of oxygen and graphitization, which makes it impossible to obtain accurate results. There has been developed, and practically used, an apparatus, mainly, for application to soil samples, which can determine nitrogen and carbon simultaneously with 0.2 to 1 g of the samples after adding a powdery oxidizing agent to samples and burning them. In this method and apparatus, however, combustion is carried out with addition of a powdery oxidizing agent to samples for making up for a deficiency of oxygen on combustion, so that error-inducing factors increase in number. Also, all of the surplus oxygen introduced by or evolved from the oxidizing agent are removed by reaction with reduced copper, so that the life of reduced copper becomes extremely short, which disadvantageously requires frequent exchange and regeneration of reduced copper.

Under these circumstances, the present inventors have extensively studied to provide an improved analytical method which has no drawbacks as in the prior art and enables independent or simultaneous determination of nitrogen, carbon, hydrogen and sulfur or chlorine in solid or liquid samples in a more rapid, simple, accurate, and high sensitive manner.

One object of the present invention is to provide an improved analytical method for the independent or simultaneous determination of any number of elements, nitrogen, carbon, hydrogen and sulfur or chlorine in solid or liquid samples in a rapid, simple, accurate, high sensitive manner. Another object of the present invention is to provide an improved analytical method for the determination of elements which is also applicable for extremely flame resistant samples. A further object of the present invention is to provide an apparatus for carrying out the above improved method. These and other objects and advantages of the present invention will be apparent from the following description.

According to the present invention, there is provided a method for the analysis of carbon, nitrogen, hydrogen and sulfur or chlorine in samples and a suitable apparatus therefor, said method comprising introducing a sample into a high-temperature oxidation catalyst or oxidizing agent layer while circulating 100% oxygen gas through the layer, whereby the sample is burned and completely oxidized into nitrogen oxides, carbon dioxide, steam and sulfur oxides, uniformalizing the resulting combustion gas by circulation, dividing the gas into two portions in a definite volume ratio, and treating the two portions as follows: The one portion is sent, together with an inert carrier gas, to a reducing agent layer to remove the oxygen gas and convert nitrogen oxides to nitrogen gas, the gas from the reducing agent layer is sent to a calcium carbide-packed tube to convert steam to acetylene gas, the gas from the tube is sent to a separation column to separate into component gases (nitrogen gas, carbon dioxide gas and acetylene gas), and these separated gases are sent to a gas analyzer for detection and determination; and the other portion, occupying the greater part of the combustion gas, is introduced, together with oxygen gas, into an absorption liquor and absorbed in the liquor, and the resulting sulfate ion or chlorine ion is detected and determined, for example, by an absorptiometric method with a flow cell.

In the present invention, detection of nitrogen gas, carbon dioxide gas and acetylene gas may be carried out by means of thermal conductivity, helium ionization or interference of light. In the use of a gas chromatograph with a thermal conductivity detector, helium or argon may be used as a carrier gas, and nitrogen, carbon dioxide and acetylene gases produced in the reaction zone may be detected. In the use of a gas chromatograph with a helium ionization detector, helium is used as a carrier gas, and nitrogen, carbon dioxide and acetylene gases produced in the reaction zone may be detected by ionizing or exciting helium by $\beta$-ray or glow discharge, thereby causing Penning's effect to ionize these gases, and electrically taking out their respective increments of ionic current generated by ionization. In the use of a photointerference gas detector, helium or argon may be used as a carrier gas, and nitrogen, carbon dioxide and acetylene gases produced in the reaction zone may be detected.

For detection of sulfur oxides, they are absorbed in an absorption liquor and detected by means of specific ion electrodes, solution electroconductivity, coulometric titration, rosaniline colorimetry or barium chloride turbidimetry. For the detection of hydrogen chloride or chlorine, they are absorbed in an absorption liquor and detected by means of specific ion electrodes, silver nitrate turbidimetry, mercuric thiocyanate colorimetry or silver chromate colorimetry.

When a quartz tube is used as a reaction tube and an oxidation catalyst is used, palladium or platinum net (wire diameter, 5–100$\mu$), or 0.1 to 3 wt.% palladium or platinum catalyst supported on 10 to 40-mesh alumina is packed in the reaction tube, and thoroughly activated by passing oxygen or air therethrough at 900° C. to 1100° C. for more than 10 hours, and it is used for reaction at a temperature of 800° C. to 1100° C. When an oxidizing agent is used, 10 to 20-mesh granular cobalt oxide, or 5 to 30 wt.% cobalt oxide supported on silica-alumina type ceramics wool (wire diameter 1–10$\mu$), as produced by impregnating the wool with an aqueous cobalt nitrate solution and heating at a temperature of from 800° C. to 1000° C., preferably from 800° C. to 900° C., in air or oxygen current, or copper oxide (wire diameter, 0.2–1 mm; length, 2–5 mm) is packed in the reaction tube and used for reaction at a temperature of 800° C. to 1000° C., preferably 800° C. to 950° C.

When the temperature of the reaction tube is less than 800° C., in case of samples such as flame-resisting organic compounds, incomplete combustion takes place, which results in lower determinability and reproducibility. Determination may be possible even when the temperature is more than 1100° C., but very expensive furnaces (in terms of material and structure) are necessary, and the material for the tube is limited. Furthermore, various problems arise such as blocking of the tube due to the fusion and solidification of copper oxide used as an oxidizing agent.

Reduction of the combustion gas may be carried out by using as a reduction tube a quartz tube packed with reduced copper and heating the tube at from 400° C. to 700° C. In this reduction tube, oxygen in the combustion gas collected in the weighing tube from the combustion system is removed, and at the same time, nitrogen oxides in the gas are reduced to nitrogen gas. When the temperature of the reduction tube is less than 400° C., the reducing power of reduced copper lowers to make normal determination of nitrogen impossible. When the temperature is more than 700° C., a part of the carbon dioxide is reduced into carbon monoxide, which results in lowering of the determinability and reproducibility of carbon content. Further, copper oxide, as produced by the reaction of reduced copper with oxygen, gradually releases oxygen at a temperature of higher than 700° C., so that normal determination sometimes becomes impossible.

For the simultaneous determination of nitrogen, carbon and hydrogen, the gas-absorbing tube is packed with calcium carbide. For the simultaneous determination of nitrogen and carbon, the tube is packed with a moisture absorber such as magnesium perchlorate or Molecular Sieve 3A, and for the determination of nitrogen alone, the tube is packed with both a moisture absorber (e.g. magnesium perchlorate, Molecular Sieve 3A) and a carbon dioxide gas absorber (e.g. soda asbestos). For the simultaneous determination of carbon and hydrogen, nitrogen gas is used as a carrier gas, and the gas-absorbing tube is packed with calcium carbide. For the determination of carbon alone, nitrogen gas is used as a carrier gas, and the tube is packed with a moisture absorber such as magnesium perchlorate or Molecular Sieve 3A. For the determination of hydrogen alone, nitrogen gas is used as a carrier gas, and the tube is packed with both calcium hydride and soda asbestos. Further, for the simultaneous determination of nitrogen and hydrogen, argon gas is used as a carrier gas, and the tube is packed with both calcium hydride and soda asbestos.

The method and apparatus of the present invention will be illustrated in more detail with reference to the accompanying drawing, wherein a gas chromatograph with a thermal conductivity detector and, for determination after absorption of the combustion gas into the absorption liquor, a spectrophotometer with a flow cell are used.

FIG. 1 is a schematic view of one embodiment of the apparatus used for the method of the present invention. 1 is a carrier gas bomb which may contain either helium or argon. The carrier gas is divided into two portions after passing through a pressure reducer 2. One portion is sent to the reference side of a gas chromatograph through a pressure regulator 5, and another portion is sent to a reduction tube 10 through a pressure regulator 4 and a combustion gas feed cock 8. An appropriate flow rate of the carrier gas is 20 to 100 ml/min. The feed cock 8 may introduce the combustion gas circulating through the combustion system, as collected in a definite volume of 1 to 5 ml by a weighing tube 33, into a carrier gas channel. An appropriate reduction tube is a transparent quartz tube of 8 to 15 mm in inside diameter and 20 to 40 cm in length. Reduced copper packed in the reduction tube 10 may be any of linear, granular and net-like product, and it is heated to 400° C. to 700° C. by a reduction furnace 11. The gas from the reduction tube 10 is sent to a gas chromatograph with a thermal conductivity detector 17 through a gas absorbing tube 13. The gas absorbing tube, as intended for complete removal of steam and/or carbon dioxide gas or conversion of steam into acetylene, may be a glass tube of 6 to 12 mm in inside diameter and of 10 to 20 cm in length. In use, it is packed with a moisture absorber (e.g. magnesium perchlorate, Molecular Sieve 3A) and/or a carbon dioxide gas absorber (e.g. soda asbestos, Ascarite), or a converting agent such as calcium carbide or calcium hydride for converting steam to acetylene gas or hydrogen gas, respectively.

The gas chromatograph may be any of a dual-column flow line form and a single-column clow line form. A packing for use in separating columns 15 and 16 may be any of those which are used in gas chromatography of common inorganic gases, for example silica gel and porous polymer beads. Singals from the thermal conductivity detector 17 are recorded on a recorder 48 through a signal line 47.

An appropriate reaction tube is a transparent quartz tube of 12 to 40 mm in inside diameter and 20 to 50 cm in length. A reaction tube 28 is equipped at the inlet side with a liquid sample feed inlet 27 to which a septum is fixed to feed a liquid sample by means of a microsyringe. For use of the tube 28, it is packed with an oxidizing agent (e.g. cobalt oxide, copper oxide) or an oxidation catalyst (e.g. palladium, platinum), and heated to 800° C. to 1100° C. by a heating furnace 29. Cobalt oxide may be of a granular form, or supported on silica-alumina type ceramics wool. Copper oxide may be any of linear, granular and net-like product. Palladium or platinum is used as the one supported on linear, net-like or granular alumina.

Oxygen gas for complete combustion of samples in the reaction tube 28 flows into an oxygen line-changing cock 23 from an oxygen bomb 18 through a pressure reducer 19 and a resisting tube 21. The flow rate of oxygen is controlled by the secondary pressure of the reducer 19 and adjustment of the tube 21, and it is preferably in the range of from 100 to 500 ml/min. The reaction tube 28 is equipped, at the oxygen inlet side, with a sample feed inlet 25 through which a sample, as placed on a boat at the tip of a sample charging rod 26, is introduced into the reactor. Boats made of platinum, nickel or quartz can be used. Because of its lower thermal conductivity, a boat made of quartz is preferably used when a large amount of readily combustible sample is applied. When a boat made of platinum or nickel having a thermal conductivity higher than the permitted range is used in the case of such a readily combustible sample, there is the possibility of incomplete combustion due to explosive combustion.

Oxygen gas is circulated by means of a circulating pump 35. The combustion gas from the tube 28 is uniformalized by circulation through the combustion system in the sequence of a gas mixing tube 31, a combustion gas feed cock 8, a weighing tube 33, a circulating pump 35, a flow meter 37, an oxygen line-changing cock 23 and a reaction tube 28. The pump 35 is preferably a diaphragm pump, and its flow rate is preferably in the range of from 200 to 1500 ml/min. The tube 31 is a glass winding tube of 6 to 20 mm in inside diameter and 20 to 300 cm in length, it accelerates uniformalization of the combustion gas and acts as a main part for reserving oxygen gas for completely burning a sample during operation of the combustion system, i.e., circulation of combustion gas through a combustion system in a closed state. As conduits 24, 30, 32, 34, 36 and 38, the weighing tube 33 and carrier gas channels 9 and 12 in the combustion system, internally Teflon- or glass-lined stainless steel pipe is used for preventing adsorption of the combustion gas. These conduits and others are used preferably at a temperature of 100° C. to 180° C.

After the combustion gas has been collected by the weighing tube 33, the remaining gas occupying the greater part of the combustion gas is introduced, together with oxygen gas, into an absorption liquor 41 in a combustion gas absorbing tube 40 through a Teflon conduit 39, whereby the liquid absorbs sulfur oxides, chlorine gas or hydrogen chloride gas to develop a color. The liquor is then sent to a spectrophotometer 43 with a flow cell by means of a microtube pump 44 to detect and determine sulfur or chlorine. The remaining waste absorption liquor is received in a receiver 46. When samples of little sulfur content are used, determination can be made by the pararosaniline method using aqueous solutions containing sodium chloride and mercuric chloride as the absorption liquor. With samples of large sulfur content, determination can be made by the barium chloranilate method or barium sulfate turbidimetry using aqueous hydrogen peroxide as the absorption liquor. Determination of chlorine can be made by the mercuric thiocyanate method or silver nitrate turbidimetry using water as the absorption liquor.

For carrying out the analysis of the present invention, the temperature-controlling section of the detection part and the reduction furnace 11 is first stabilized while maintaining the flow of carrier gas as shown in FIG. 1. Then, the oxygen line-changing cock 23 is operated to form oxygen flow through conduits 22 and 24, thereby stabilizing the temperature of the heating furnace 29. In this state, the sample feed inlet 25 is opened, the charging rod 26 is taken out, the boat carrying a sample is placed on the tip of the rod and inserted into the reaction tube 28 so that it is situated at the site which has been cooled by an air-cooled tube 50 connected to an air pump 49. Thereafter, the feed inlet 25 is sealed, and the combustion system is allowed to stand for a few minutes to completely replace its atmosphere with oxygen. The cock 23 is operated to form the gas flow as shown in FIG. 1, and oxygen is circulated through the combustion system by means of a circulating pump 35. The charging rod 26 is then inserted into the reaction tube 28 so that the boat is situated at the center of the furnace, thereby subjecting the sample to complete combustion, and the produced combustion gas and excess oxygen gas are circulated through the combustion system to uniformalize the mixed gas. The combustion gas feed cock 8 is operated so that the carrier gas flows through the conduit 6, weighing tube 33 and the conduit 9 in sequence, thereby sending the combustion gas in the weighing tube 33 to the reduction tube 10, at which oxygen gas is completely removed and nitrogen oxides are reduced into nitrogen gas. After the gas from the tube 10 is, if necessary, passed through the gas absorbing tube 13 to convert steam in the gas to acetylene gas, it is separated into component gases, nitrogen, carbon dioxide and acetylene gases in separating columns 15 and 16, and each gas is detected and determined on the thermal conductivity detector 17.

Immediately after introducing the combustion gas in the weighing tube 33 into the carrier gas channel, the cock 23 is operated so that oxygen flows through conduits 22 and 24 in sequence. By this operation, the remaining combustion gas in the combustion system is introduced into the absorption liquor 41, whereby the liquor absorbs sulfur oxides or chlorine in the gas. Sulfur or chlorine in the liquor may be detected and determined by means of specific ion electrodes, or, after the liquor has been color-developed or made turbid, by measuring the absorbance of the liquor by means of a spectrophotometer with a flow cell. Operation of the cocks 8 and 23 can be carried out using a micro-switch and a solenoid motor, whereby the flow direction of the combustion gas and oxygen can be changed. The foregoing carrier gas feed part, oxygen gas feed part, sample feed part, reaction part in combustion system, gas circulation part in combustion system, combustion gas feed part, reduction part, gas absorption part, gas separation part, gas detection part, combustion gas absorption part and absorptiometric detection part with flow cell are connected by conduits 3, 6, 7, 9, 12, 14, 20, 22, 24, 30, 32, 34, 36, 38, 39, 42 and 45.

The present invention will be illustrated with reference to the following examples, which are not, however, to be interpreted as limiting the invention thereto.

EXAMPLE 1

Simultaneous determination of nitrogen, carbon, hydrogen and sulfur in various nitrogen/sulfur-containing organic compounds was carried out under the following conditions using the apparatus as shown in FIG. 1.

A transparent quartz tube (30 mm in outside diameter, 26 mm in inside diameter and 35 cm in length) was used as a reaction tube, and it was packed with zones of quartz cotton (diameter, 1–6μ), 10 to 24-mesh granular cobalt oxide and quartz cotton (diameter, 1–6μ) in this sequence with the former zone located at the gas outlet of the tube, so that the length of each zone was about 40 mm, about 100 mm and about 20 mm, respectively. The reaction tube was then heated to 900° C. in the heating furnace of 20 cm in length.

A transparent quartz tube (15 mm in outside diameter, 10 mm in inside diameter and 25 cm in length) was used as a reduction tube, and it was packed with a zone of linear reduced copper (diameter, 0.6 mm∅; length 2–4 mm) in the middle of it so that the length of the zone was 19 cm, wherein the zone of linear reduced copper was fixed at both ends in a length of 30 mm with a quartz cotton zone (cotton diameter, 1–6μ). The reduction tube was heated to 550° C. in a reduction furnace of 22 cm in length.

A glass winding tube (18 mm in inside diameter and 200 cm in length) was used as a gas mixing tube, and an internally glass-lined stainless steel tube of 3 ml in volume was used as a weighing tube. Internally glass-lined stainless steel tubes were used as conduits 9, 12, 24, 30, 32, 34, 36 and 38, and they were heated to 150° C. on using.

A glass straight tube (8 mm in inside diameter and 10 cm in length) was used as a gas-absorbing tube, and it was packed with a zone of 10 to 20-mesh calcium carbide in the middle of it so that the length of the zone was 8 cm, wherein the zone of calcium carbide was fixed at the both ends in a length of 10 mm with a quartz cotton zone (cotton diameter, 1–6μ).

A stainless steel column (3 mm in inside diameter and 1 m in length) was used as a separating column of gas chromatograph, and it was packed with 60 to 80-mesh silica gel. Helium was used as a carrier gas, and it was streamed at a rate of 70 ml/min. The temperature of the thermal conductivity detector was 100° C., and the bridge current was 125 mA.

A stainless steel tube (2 mm in inside diameter and 1 m in length) was used as a resisting tube, and it was packed with 100 to 180 mesh quartz particles. The flow rate of oxygen gas was 400 ml/min, and that of the circulating gas through a diaphragm pump was adjusted to 500 ml/min. Barium chloride (10 g), sodium chloride (50 g), glycerin (20 g) 1 N hydrochloric acid (10 ml) and 30% aqueous hydrogen peroxide (50 ml) were dissolved in distilled water and made up to 500 ml with distilled water. Fifty milliliters of this absorption liquor was placed in the combustion gas-absorbing tube (volume, 100 ml). After absorption of sulfur oxides in the liquor, the produced barium sulfate-turbid liquor was measured for absorbance at a wave length of 400 nm, while passing the liquor at a rate of 20 ml/min through a flow cell of 1 cm in light-pass length by means of a microtube pump.

5 to 50 mg of sulfathiazole, a reagent for elementary analysis, was accurately weighed into a platinum boat using a semimicro balance, and the boat was placed on the tip of a charging rod and set in position in the reaction tube. Thereafter, oxygen gas was passed through the combustion system for 2 minutes to completely replace the atmosphere of the system with oxygen. After shutting the oxygen flow through conduits 22 and 24 by operating the oxygen flow-changing cock, the boat was inserted into high-temperature zone of the reaction tube to subject the sample to complete combustion, while circulating oxygen gas through the system by the circulating pump. The combustion gas thus produced was uniformalized by circulation for 2 minutes, and then the combustion gas feed cock was operated to send the gas in the weighing tube to the column through the reduction tube and gas absorbing tube in sequence.

Figure 2:
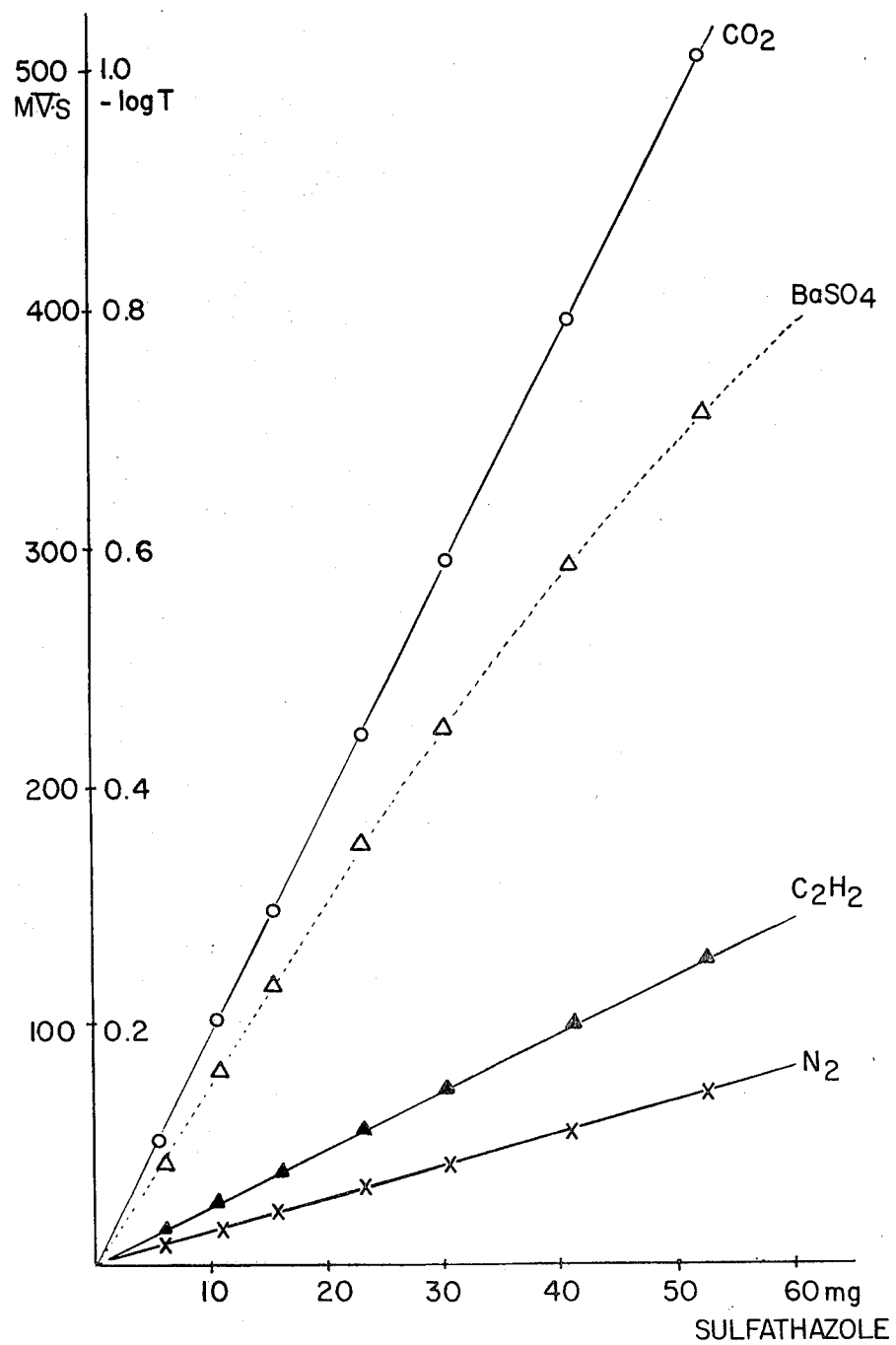

The peak areas of nitrogen, carbon dioxide and acetylene gases were obtained by integral, and relationship between these peak areas annd the contents of nitrogen, carbon and hydrogen of the sample was obtained. Further, the absorbance of the absorption liquor which has absorbed the combustion gas was measured, and relationship between the absorbance and the sulfur content of the sample was obtained. The results are shown in Table 1. These relationships were plotted to obtain straight lines and curves as shown in FIG. 2, wherein the lines were obtained by plotting the peak area (integral value) of $N_2$, $CO_2$ and $C_2H_2$ against each amount of the sample (sulfathiazole) as shown in Table 1, and by plotting the absorbances of $BaSO_4$-turbid liquor against the same amounts of the sulfathiazole. FIG. 3 shows a chromatogram expressing peaks of $N_2$, $CO_2$ and $C_2H_2$ measured at a full scale of 64 mV with 30.62 mg of sulfathiazole, a reagent for elementary analysis. Further, elementary analysis was made with accurately weighed 20 to 40 mg of various nitrogen/sulfur containing organic compounds of elementary analysis grade and special grade, using said sulfathiazole as standard. The results are shown in Table 2.

TABLE 1

| Amount of sample (mg) | Integral value for $N_2$ (μV.S) | Integral value for $CO_2$ (μV.S) | Integral value for $C_2H_2$ (μV.S) | Absorbance (−log T) |
|---|---|---|---|---|
| 52.88 | 70216 | 507083 | 126974 | 0.714 |
| 41.39 | 55159 | 397098 | 99497 | 0.585 |
| 30.62 | 40757 | 293991 | 73498 | 0.425 |
| 23.25 | 30939 | 222469 | 54650 | 0.349 |
| 15.46 | 20813 | 148720 | 37712 | 0.233 |
| 10.71 | 14812 | 102846 | 25127 | 0.164 |
| 5.58 | 7590 | 53705 | 13189 | 0.087 |
| 0 | 442 | 117 | 296 | 0.005 |

TABLE 2

| Sample | Amount of sample (mg) | N content (%) Cal. | F. | C content (%) Cal. | F. | H content (%) Cal. | F. | S content (%) Cal. | F. |
|---|---|---|---|---|---|---|---|---|---|
| Sulfanylamide | 20.35 | 16.27 | 16.25 | 41.85 | 41.84 | 4.68 | 4.62 | 18.62 | 18.5 |
| $C_6H_8O_2N_2S$ | 31.82 | 16.27 | 16.40 | 41.85 | 41.89 | 4.68 | 4.65 | 18.62 | 18.4 |
| | 36.44 | 16.27 | 16.29 | 41.85 | 41.83 | 4.68 | 4.59 | 18.62 | 18.7 |
| Thiourea | 18.43 | 36.80 | 36.69 | 15.78 | 15.80 | 5.30 | 5.42 | 42.12 | 42.1 |
| $CH_4N_2S$ | 22.37 | 36.80 | 36.77 | 15.78 | 15.83 | 5.30 | 5.37 | 42.12 | 42.4 |
| | 34.25 | 36.80 | 36.72 | 15.78 | 15.70 | 5.30 | 5.33 | 42.12 | 42.2 |
| p-Toluene- | 21.48 | 8.18 | 8.20 | 49.10 | 49.07 | 5.30 | 5.37 | 18.73 | 18.6 |
| sulfonamide | 29.73 | 8.18 | 8.15 | 49.10 | 49.03 | 5.30 | 5.14 | 18.73 | 18.9 |
| $C_7H_9O_2NS$ | 38.85 | 8.18 | 8.16 | 49.10 | 49.02 | 5.30 | 5.22 | 18.73 | 18.7 |
| sym-Diphenyl- | 19.78 | 12.27 | 12.35 | 68.39 | 68.43 | 5.30 | 5.39 | 14.04 | 13.9 |
| thiourea | 25.66 | 12.27 | 12.19 | 68.39 | 68.30 | 5.30 | 5.21 | 14.04 | 14.2 |
| $C_{13}H_{12}N_2S$ | 37.21 | 12.27 | 12.24 | 68.39 | 68.36 | 5.30 | 5.23 | 14.04 | 14.0 |

Cal.: Calculated
F.: Found

EXAMPLE 2

Simultaneous determination of nitrogen, carbon and chlorine was made using 2,4-dinitrochlorobenzene, a reagent for elementary analysis, as standard. 2 to 5 mg of chlorine-containing organic compounds was accurately weighed into a platinum boat using a micro-balance. For analysis of chlorine, chlorine and hydrogen chloride in the combustion gas were absorbed in 50 ml of 0.1 N aqueous sodium hydroxide solution, an absorption liquor, and then the solution was measured for chlorine ion using a specific ion electrode.

Other analytical conditions were the same as in Example 1 except that a transparent quartz tube (30 mm in outside diameter, 26 mm in inside diameter and 35 mm in length) was used as a reaction tube, and it was packed with zones of quartz cotton (cotton diameter, 1–6μ), 0.5% palladium catalyst supported on 10 to 20-mesh alumina, and quartz cotton (cotton diameter, 1–6μ) in this sequence with the former zone located at the gas outlet of the tube, so that the length of each zone was about 40 mm, 100 mm and about 20 mm, respectively, and the reaction tube was then heated to 950° C. in the heating furnace of 20 cm in length; a glass tube (8 mm in inside diameter and 50 cm in length) was used as a gas-mixing tube; and a glass straight tube (8 mm in inside diameter and 10 cm in length) was used as a gas absorbing tube, and it was packed with a zone of 10 to 20-mesh magnesium perchlorate in the middle of it so that the length of the zone was 8 cm, wherein the zone of magnesium perchlorate was fixed at the both ends in a length of 10 mm with a quartz cotton zone (cotton diameter, 1–6μ). The results are shown in Table 3.

TABLE 3

| Sample | Amount of sample (mg) | N content (%) Cal. | F. | C content (%) Cal. | F. | Cl content (%) Cal. | F. |
|---|---|---|---|---|---|---|---|
| 2,4-Dichloro- | 2.382 | 0.00 | 0.00 | 43.47 | 43.54 | 32.08 | 31.8 |
| phenoxyacetic | 3.526 | 0.00 | 0.00 | 43.47 | 43.49 | 32.08 | 31.4 |
| acid | 4.379 | 0.00 | 0.00 | 43.47 | 43.40 | 32.08 | 32.2 |
| $C_8H_6O_3Cl_2$ | | | | | | | |
| m-Nitrochloro- | 1.974 | 8.89 | 8.75 | 45.74 | 45.70 | 22.50 | 22.7 |
| benzene | 3.045 | 8.89 | 8.86 | 45.74 | 45.76 | 22.50 | 22.4 |
| $C_6H_4O_2NCl$ | 4.748 | 8.89 | 8.83 | 45.74 | 45.68 | 22.50 | 22.1 |
| Homosulfamine | 2.935 | 12.58 | 12.63 | 37.75 | 37.90 | 15.92 | 16.2 |
| $C_7H_{10}O_2N_2S.HCl$ | 3.610 | 12.58 | 12.59 | 37.75 | 37.71 | 15.92 | 15.6 |
| | 5.174 | 12.58 | 12.54 | 37.75 | 37.72 | 15.92 | 16.0 |

EXAMPLE 3

20 to 500 mg of samples to be analyzed was accurately weighed into a platinum boat using a direct-reading balance having a readability of 0.1 mg, and determined for nitrogen content alone using acetanilide, a reagent for elementary analysis, as standard.

Other analytical conditions were the same as in Example 1 except that a transparent quartz tube (30 mm in outside diameter, 26 mm in inside diameter and 35 cm in length) was used as a reaction tube, and it was packed with zones of quartz cotton (diameter, 1–6μ), 1% platinum catalyst supported on 10 to 20-mesh alumina and quartz cotton (diameter, 1–6μ) in this sequence with the former zone located at the gas outlet of the tube, so that the length of each zone was about 40 mm, about 100 mm and about 20 mm, respectively, and the reaction tube was heated to 950° C. in the heating furnace of 20 cm in length; a glass straight tube (8 mm in inside diameter and 15 cm in length) was used as a gas-absorbing tube, and it was packed with zones of 10 to 20-mesh magnesium perchlorate, absorbent cotton and 10 to 20-mesh soda asbestos in this sequence with the former zone located at the gas inlet of the tube, so that the length of each zone was 60 mm, 10 mm and 60 mm, respectively; and this continuous zone was fixed with absorbent cotton at the both ends.

In order to confirm the reliability of the analytical values obtained, comparison with those obtained by the marco-Kjeldahl method was made. The results are shown in Table 4.

TABLE 4

| Sample | Amount of sample (mg) | Nitrogen content (%) No. 1 | No. 2 | No. 3 | Average | Nitrogen content by Kjeldahl method (%) |
|---|---|---|---|---|---|---|
| Polymer (A) | 20–30 | 1.74 | 1.81 | 1.77 | 1.77 | 1.76 |
| Polymer (B) | 60–80 | 0.0351 | 0.0344 | 0.0329 | 0.0341 | 0.033 |
| Oil and fat (A) | 40–60 | 0.149 | 0.140 | 0.146 | 0.145 | 0.140 |
| Oil and fat (B) | 60–80 | 0.0603 | 0.0608 | 0.0594 | 0.0602 | 0.059 |
| Saccharide (A) | 40–50 | 0.153 | 0.168 | 0.165 | 0.162 | 0.167 |
| Saccharide (B) | 70–80 | 0.0209 | 0.0201 | 0.0210 | 0.0207 | 0.020 |
| Coffee (A) | 20–30 | 3.15 | 3.12 | 3.14 | 3.14 | 3.14 |
| Coffee (B) | 20–30 | 1.00 | 1.05 | 1.03 | 1.03 | 1.04 |
| Unpolished rice (A) | 20–30 | 1.56 | 1.59 | 1.54 | 1.56 | 1.58 |
| Unpolished rice (B) | 20–30 | 1.31 | 1.24 | 1.27 | 1.27 | 1.28 |
| Soil (A) | 300–500 | 0.201 | 0.193 | 0.195 | 0.196 | 0.196 |
| Soil (B) | 400–500 | 0.0623 | 0.0621 | 0.0608 | 0.0617 | 0.061 |

EXAMPLE 4

30 to 40 mg of various heavy oils was accurately weighed into a platinum boat using a direct-reading balance having a readability of 0.1 mg, and simultaneous determination of nitrogen and sulfur contents was made using sulfathiazole, a reagent for elementary analysis, as standard.

Other analytical conditions were the same as in Example 1 except that a transparent quartz tube (30 mm in outside diameter, 26 mm in inside diameter and 35 cm in length) was used as a reaction tube, and it was packed with zones of quartz cotton (diameter, 1–6μ), linear copper oxide (diameter, 0.6 mmØ; length, 2–4 mm) and quartz cotton (diameter, 1–6μ) in this sequence with the former zone located at the gas outlet of the tube, so that the length of each zone was about 40 mm, about 100 mm and about 20 mm, respectively, and the reaction tube was heated to 900° C. in the heating furnace of 20 cm in length; a glass straight tube (8 mm in inside diameter and 15 cm in length) was used as gas-absorbing tube, and it was packed with zones of 10 to 20-mesh magnesium perchlorate, absorbent cotton and 10 to 20-mesh soda asbestos in this sequence with the former zone located at the gas inlet of the tube, so that the length of each zone was 60 mm, 10 mm and 60 mm, respectively; and this continuous zone was fixed with absorbent cotton at the both ends.

In order to confirm the reliability of the analytical values obtained, comparison with those of nitrogen content by the macro-Kjeldahl method and those of sulfur content by the method in JIS K-2541, Testing Method for Sulfur in Petroleum Products by Quartstube Combustion (Air method), was made. The results are shown in Table 5.

TABLE 5

| Sample | Nitrogen content (%) Present method No. 1 | Nitrogen content (%) Present method No. 2 | Kjeldahl method | Sulfur content (%) Present method No. 1 | Sulfur content (%) Present method No. 2 | JIS method |
|---|---|---|---|---|---|---|
| Heavy oil (A) | 0.153 | 0.160 | 0.151 | 1.07 | 1.11 | 1.10 |
| Heavy oil (B) | 0.0760 | 0.0753 | 0.074 | 0.461 | 0.465 | 0.46 |
| Heavy oil (C) | 0.212 | 0.203 | 0.210 | 1.42 | 1.39 | 1.45 |
| Heavy oil (D) | 0.0321 | 0.0339 | 0.031 | 0.360 | 0.362 | 0.36 |
| Heavy oil (E) | 0.273 | 0.282 | 0.273 | 1.86 | 1.79 | 1.85 |
| Heavy oil (F) | 0.118 | 0.120 | 0.118 | 0.953 | 0.950 | 0.97 |
| Heavy oil (G) | 0.0504 | 0.0500 | 0.051 | 0.093 | 0.094 | 0.09 |
| Heavy oil (H) | 0.0211 | 0.0206 | 0.021 | 0.052 | 0.053 | 0.05 |

EXAMPLE 5

Simultaneous determination of nitrogen and carbon of liquid samples was made using acetanilide, a reagent for elementary analysis, as standard. 20 μl of aqueous or ethyl alcoholic solution of each nitrogen-containing organic compounds was added dropwise to a quartz boat through a liquid sample feed inlet using a microsyringe, and the boat on the tip of a charging rod was set at a high temperature position in the reaction tube. Thereafter, the combustion gas produced was uniformalized by circulation for 1 minute, and then, the determination was done. The results are shown in Table 6.

Other analytical conditions were the same as in Example 1 except that a transparent quartz tube (18 mm in outside diameter, 15 mm in inside diameter and 50 cm in length) with a liquid sample feed inlet was used as a reaction tube, and it was packed with zones of quartz cotton (diameter, 1–6μ), linear copper oxide (diameter, 0.6 mm; length, 2–5 mm) and quartz cotton (diameter, 1–6μ) in this sequence with the former zone located at the gas outlet of the tube, so that the length of each zone was about 35 mm, about 240 mm and about 20 mm, respectively, and the reaction tube was heated to 900° C. in the heating furnace of 35 cm in length; a U-tube (10 mm in inside diameter and 15 ml in volume) was used as a gas mixing tube; and a glass straight tube (8 mm in inside diameter and 10 cm in length) was used as a gas-absorbing tube, and it was packed with 10 to 20-mesh magnesium perchlorate in the center zone of 8 cm length, which was fixed with quartz cotton (diameter, 1–6μ) in a length of 10 mm at the both ends. The results are shown in Table 6.

TABLE 6

| Sample | Solvent | N content (%) Cal. | N content (%) F. | C content (%) Cal. | C content (%) F. |
|---|---|---|---|---|---|
| Glycine | water | 0.187 | 0.181 | 0.320 | 0.319 |
| Ammonium oxalate | water | 0.197 | 0.196 | 0.169 | 0.169 |
| Acetoxime | water | 0.192 | 0.194 | 0.493 | 0.496 |
| N—Acetylglycine | water | 0.012 | 0.011 | 0.041 | 0.040 |
| Hexamethylene-tetramine | water | 0.040 | 0.040 | 0.051 | 0.050 |
|  | ethyl alcohol | 0.022* | 0.021 | 52.1 | 52.0 |
| P-Nitroaniline | ethyl alcohol | 0.249 | 0.253 | 52.1 | 52.1 |

[Note]:
*In case of using ethyl alcohol only, the calculated N content was the amount existed in solubilized form.

EXAMPLE 6

Simultaneous determination of nitrogen and carbon contained in extremely flame-resistant samples: carbon fiber and graphite was made using acetanilide, a reagent for elementary analysis, as standard.

Other analytical conditions were the same as in Example 5 except that 5 to 8 mg of samples was accurately weighed into a quartz boat using a micro balance; the boat on the tip of a charging rod was set in the high temperature zone, without circulation of oxygen gas; the still combustion was carried out for 3 minutes in case of carbon fiber and for 15 minutes in case of graphite; and thereafter, the combustion gas produced was uniformalized by circulation for 1 minute, and then the determination was done. The results are shown in Table 7.

TABLE 7

| Sample | N content (%) 1 | N content (%) 2 | N content (%) Av. | C content (%) 1 | C content (%) 2 | C content (%) Av. |
|---|---|---|---|---|---|---|
| Carbon Fiber (1) | 4.49 | 4.54 | 4.52 | 95.27 | 95.12 | 95.20 |
| Carbon Fiber (2) | 7.62 | 7.61 | 7.62 | 92.01 | 91.99 | 92.00 |
| Carbon Fiber (3) | 6.12 | 6.11 | 6.11 | 93.20 | 93.35 | 93.28 |
| Graphite | 0.013 | 0.015 | 0.014 | 99.95 | 99.89 | 99.92 |

Three kinds of carbon fibers supplied for elementary determination were made from polyacrylonitrile fiber. The carbon products such as carbon fiber or graphite prepared by calcining the precursor at 1,000° C. or higher. The elementary determination of such carbon products can not be done directly by prior technique. Therefore, quantitative comparison of performance in elementary determination between this invention's method and others is impossible. But, the results by this method are considered to be reasonable, when they are estimated based upon the amount and composition of the gases produced during the carbonization (calcination) process of preparing carbon products.

The analytical method and apparatus of the present invention, as described above, have the following various advanges.

Analytical values with high accuracy and precision can be obtained even by sampling on direct-reading balances having a readability of 0.1 mg, because combustion of samples is carried out in circulating (or in still state) 100% oxygen gas in the presence of an oxidation catalyst or oxidizing agent, and hence, even flame-resistant samples and a large amount of sample can be subjected to complete combustion. Samples in a very wide weight range of from 1 mg to 100 mg can also be determined without lowering in sensitivity by changing the volume of the gas-mixing tube. Moreover, a very wide range of the content of elements (C, H, N), e.g. high contents of percent order to trace contents of several ten ppm order, can be analyzed. That is, according to the present invention, the combustion gas in the weighing tube can be introduced into the detector together with a carrier gas, while maintaining a limited very small volume (corresponding to the volume of the tube) with a high concentration, and hence, the determination can be made with sensitivity about 100 times higher than the conventional C.H.N. analyzers. Determination of any number of required elements can be made by proper combination of a suitable carrier gas and a suitable material to be packed in the gas absorbing tube, as shown in Table 8.

TABLE 8

| Element to be determined | Carrier gas | Packings in the gas absorbing tube |
|---|---|---|
| N, C, H | He or Ar | Calcium carbide |
| N, C | He or Ar | Magnesium perchlorate |
| N | He or Ar | Magnesium perchlorate + soda asbestos |
| C, H | $N_2$ | Calcium carbide or calcium hydride |
| C | $N_2$ | Magnesium perchlorate |
| H | $N_2$ | Calcium hydride + soda asbestos |
| N, H | He or Ar | Calcium hydride + soda asbestos |

Besides, extremely small nitrogen contents in a trace region can also be determined with a high sensitivity by the absorptiometric method with Saltzman's absorption liquor, because most of the nitrogen oxides in the combustion gas are oxidized into nitrogen dioxide by circulation together with oxygen gas. Furthermore, any number, including one or all, of the elements nitrogen, carbon, hydrogen and sulfur or chlorine can simultaneously be determined cheaply, safely, simply, rapidly and accurately, because the method of the present invention can employ a spectrophotometer and a thermal conductivity type gas chromatograph which is one of the most popularly used analyzers for gas detection.

What is claimed is:

1. A method for elementary analysis by independent or simultaneous determination of any number of elements from the group consisting of nitrogen, carbon, and hydrogen and at least one element of sulfur or chlorine in samples, comprising:
    passing an oxygen gas through a combustion system in a reaction tube packed with an oxidation catalyst or oxidizing agent having a heating zone maintained at a temperature of from 800° C. to 1100° C.;
    introducing a sample into said reaction tube with circulating oxygen in a closed system, said oxygen being present in an amount sufficient to thereby subject said sample to complete combustion and said circulating oxygen uniformalizing the resulting combustion gas by continuous circulation during combustion to achieve a homogeneous combustion gas mixture;
    dividing the homogeneous combustion gas mixture into first and second combustion portions in a definite volume ratio;
    introducing said first combustion portion, together with a carrier gas, into a reduction tube packed with reduced copper having a heating zone maintained at a temperature of from 400° C. to 700° C., and detecting and determining the resulting nitrogen gas, carbon dioxide gas and steam or acetylene gas or hydrogen gas produced by contacting steam with calcium carbide or calcium hydride; while
    introducing sulfur oxide or chlorine and/or hydrogen chloride gas contained in said second combustion mixture into an absorption liquor together with oxygen gas; and
    detecting and determining at least one of the resulting sulfate or chloride ion.

2. A method for elementary analysis according to claim 1, wherein the oxidation catalyst is palladium or platinum.

3. A method for elementary analysis according to claim 1, wherein the detection of nitrogen gas, carbon dioxide gas, and acetylene gas is performed by thermal conductivity, helium ionization or photointerference techniques.

4. A method for elementary analysis according to claim 1, wherein the detection of sulfur oxides is performed by specific ion electrodes, solution electroconductivity, coulometric titration, rosaniline colorimetry or barium chloride turbidimetry techniques, and the detection of hydrogen chloride or chlorine is performed by specific ion electrodes, silver nitrate turbidimetry, mercuric thiocyanate colorimetry or silver chlorate colorimetry techniques.

5. A method for elementary analysis according to claim 1, wherein the oxidizing agent is cobalt oxide or copper oxide.

6. A method for elementary analysis according to claim 5, wherein the oxidizing agent is used and at a temperature of from 800° C. to 950° C.

7. An apparatus for elementary analysis by independent or simultaneous determination of any number of elements from the group consisting of nitrogen, carbon and hydrogen and at least one element of sulfur or chlorine in samples comprising:
    a closed combustion system for combusting a sample to be analyzed, said closed combustion system including a gas recirculation means for continuous circulation of gases contained within the combustion system, thereby uniformalizing the resulting combustion gas to achieve a homogeneous gas mixture;
    an oxygen gas line-changing means for selectively alternating an oxygen gas feed to said combustion means in a closed system or to an absorption means;
    a combustion gas division means for dividing the homogeneous combustion gas mixture into first and second combustion portions in a definite volume ratio and simultaneously introducing said first combustion portion of the homogeneous combustion gas mixture into a carrier gas;
    a reduced copper-packed reduction means for reducing nitrogen oxides contained in the mixture of said first combustion portion and said carrier gas to nitrogen gas and simultaneously removing oxygen gas;
    a gas separation means for separating the resulting gas;
    a gas detection means for detecting gas thus separated;
    a combustion gas absorption means for absorbing and collecting sulfur oxide or chlorine and/or hydrogen chloride gas contained in said second combustion portion; and
    an absorbed gas detection means for detecting gases thus absorbed in said gas absorption means.

8. An apparatus for elementary analysis as in claim 7, wherein a gas absorption means is provided between said reduction means and said gas separation means, said gas absorption means comprising a tube packed with at least one member selected from the group consisting of a moisture absorber, a carbon dioxide gas absorber, and a converting agent for converting steam to acetylene gas or hydrogen gas.

9. An apparatus for elementary analysis as in claim 8, wherein said absorption means is packed with at least one member selected from the group consisting of calcium carbide, calcium hydride, magnesium perchlorate, and soda asbestos.

10. An apparatus for elementary analysis as in claim 7, wherein said closed combustion system includes as a combustion means a reaction tube packed with an oxidizing agent or an oxidation catalyst.

11. An apparatus for elementary analysis as in claim 10, wherein said oxidizing agent is cobalt oxide or copper oxide, or said oxidation catalyst is palladium or platinum.

12. An apparatus for elementary analysis as in claim 7, wherein said combustion gas absorption means comprises an absorption liquor.

13. An apparatus for elementary analysis as in claim 12, wherein said absorption liquor comprises aqueous solutions containing sodium chloride and mercuric chloride, aqueous hydrogen peroxide, or water.

* * * * *